(12) United States Patent
Elmi Dawale et al.

(10) Patent No.: US 11,828,701 B2
(45) Date of Patent: Nov. 28, 2023

(54) DEVICE AND METHOD FOR DETECTING CHEMICAL OR BIOLOGICAL SPECIES

(71) Applicant: COMMISSARIAT A L'ENERGIE ATOMIQUE ET AUX ENERGIES ALTERNATIVES, Paris (FR)

(72) Inventors: Houssein Elmi Dawale, Grenoble (FR);
Franck Badets, Grenoble (FR);
Sébastien Hentz, Grenoble (FR);
Guillaume Jourdan, Grenoble (FR);
Marc Sansa Perna, Grenoble (FR);
Loïc Sibeud, Grenoble (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 0 days.

(21) Appl. No.: 17/952,125

(22) Filed: Sep. 23, 2022

(65) Prior Publication Data
US 2023/0098563 A1 Mar. 30, 2023

(30) Foreign Application Priority Data

Sep. 24, 2021 (FR) ...................................... 2110087

(51) Int. Cl.
*G01N 21/17* (2006.01)
(52) U.S. Cl.
CPC ............... *G01N 21/1702* (2013.01); *G01N 2201/06113* (2013.01)
(58) Field of Classification Search
CPC ..... G01N 21/1702; G01N 2201/06113; G01N 33/54373; G01N 21/7746; B82Y 15/00; B82Y 20/00; G02B 2006/12138
See application file for complete search history.

(56) References Cited

U.S. PATENT DOCUMENTS

| 9,612,458 B1 | 4/2017 | Lentine et al. |
| 2012/0182552 A1 | 7/2012 | Heidrich et al. |

(Continued)

FOREIGN PATENT DOCUMENTS

| EP | 2 515 099 A1 | 10/2012 |
| WO | 01/63336 A1 | 8/2001 |

OTHER PUBLICATIONS

Kim, et al., "A Temperature Controller IC for Maximizing Si Micro-Ring Modulator Optical Modulation Amplitude", Journal of Lightwave Technology, vol. 37, Issue: 4, 2019.

*Primary Examiner* — Suman K Nath
(74) *Attorney, Agent, or Firm* — BakerHostetler

(57) ABSTRACT

A detecting device configured to detect chemical or biological species in a given environment, includes a matrix-array sensor formed from opto-mechanical discs that are optically and mechanically resonant, able to bind to species of the environment, and arranged in rows and columns. The opto-mechanical discs of a given row are optically coupled to the same optical waveguide. Actuating electrodes are provided in order to ensure the mechanical resonance of the opto-mechanical discs. One p-n junction is associated with each opto-mechanical disc, the junctions of a given column being electrically connected to the same biasing electrode, so as to block the flow through the corresponding opto-mechanical disc of a parasitic electrical current. A control circuit is configured to forward bias, during a time window of readout of a disc of interest, the p-n junction of a disc of interest so as to place, via a thermo-optical effect, its resonant wavelength at a working wavelength, such that an optical signal propagating through the optical waveguide associated with the disc of interest is amplitude modulated.

14 Claims, 10 Drawing Sheets

(56) References Cited

U.S. PATENT DOCUMENTS

| | | | |
|---|---|---|---|
| 2013/0293898 A1* | 11/2013 | Heck | G01C 19/661 356/460 |
| 2014/0003761 A1 | 1/2014 | Dong | |
| 2016/0069686 A1* | 3/2016 | Lee | G01C 19/5691 356/460 |
| 2016/0246000 A1* | 8/2016 | Duraffourg | G02B 6/3536 |
| 2022/0035225 A1* | 2/2022 | Aksyuk | G02B 6/3536 |

* cited by examiner

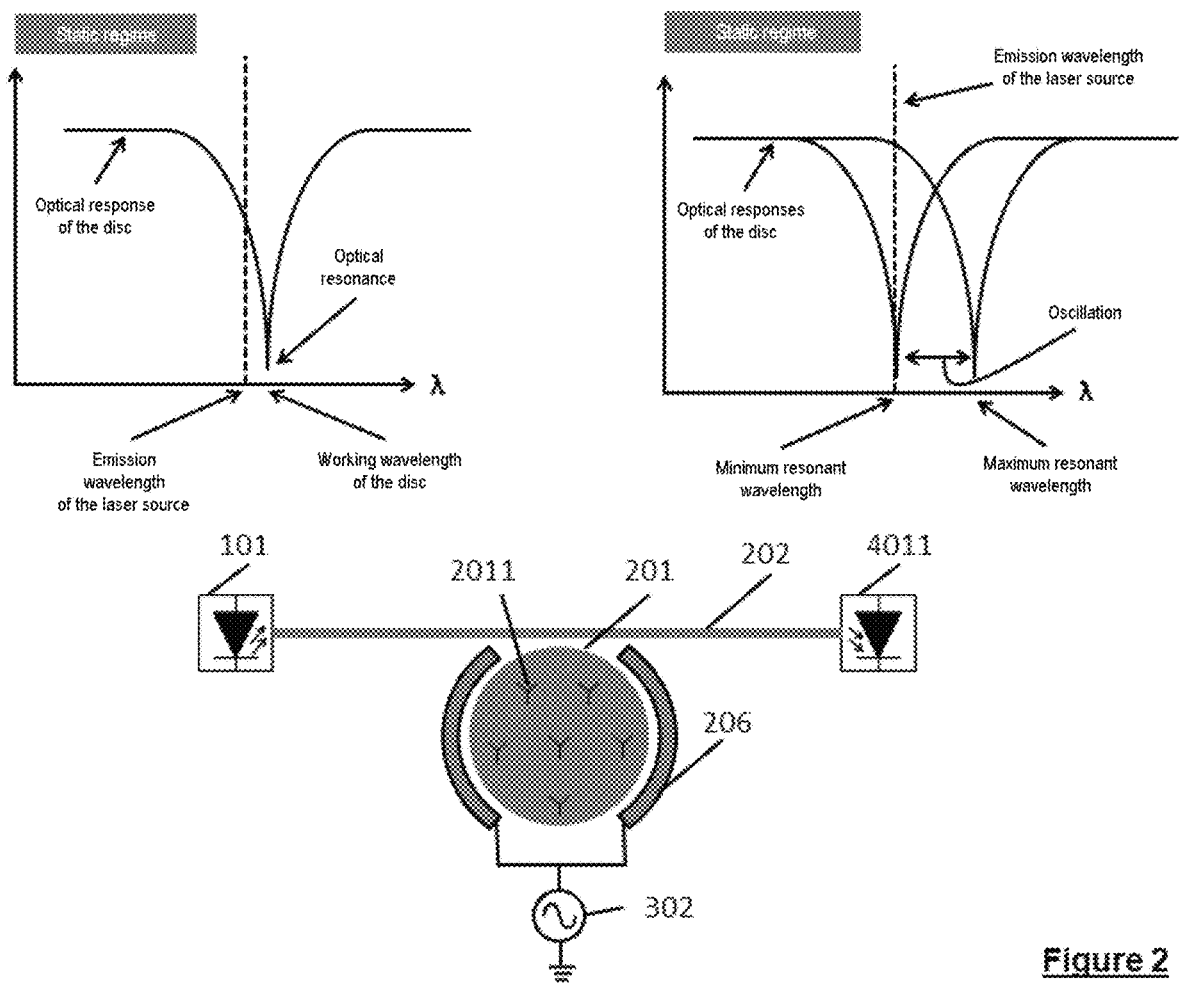
Figure 2
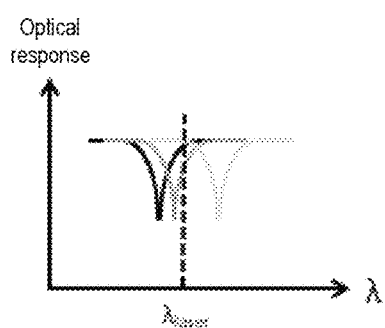
Figure 3-A

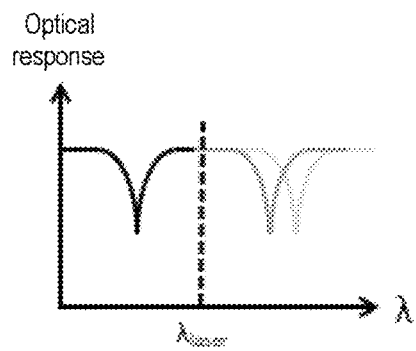
Figure 3-B
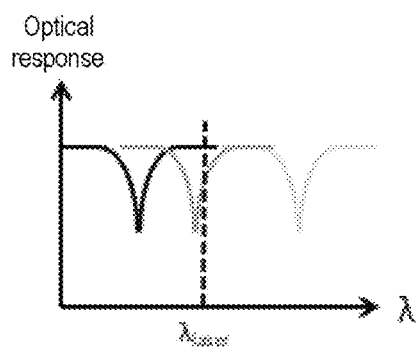
Figure 3-C
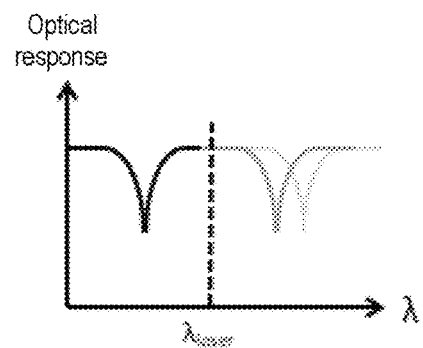
Figure 3-D

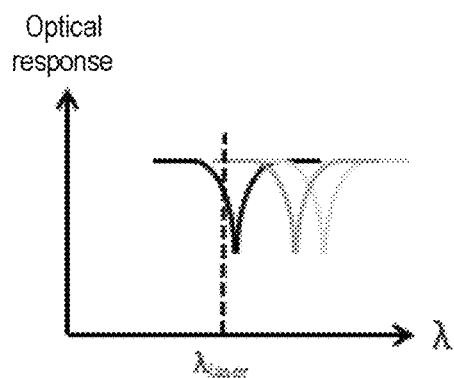
Figure 3-E
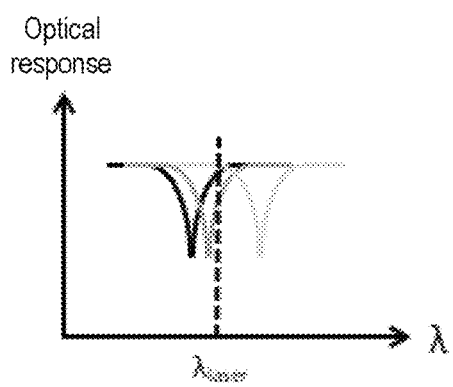
Figure 4-A
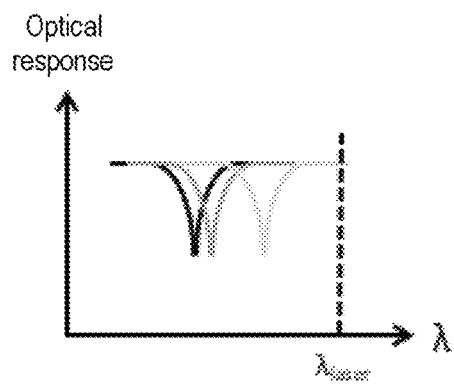
Figure 4-B

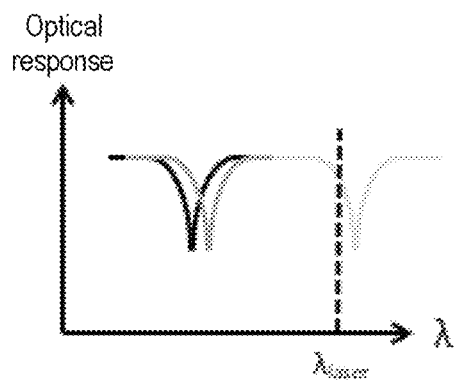
Figure 4-C
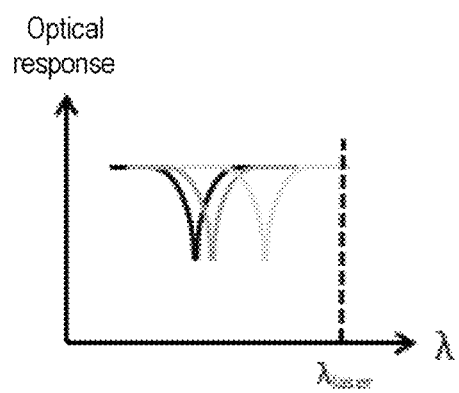
Figure 4-D

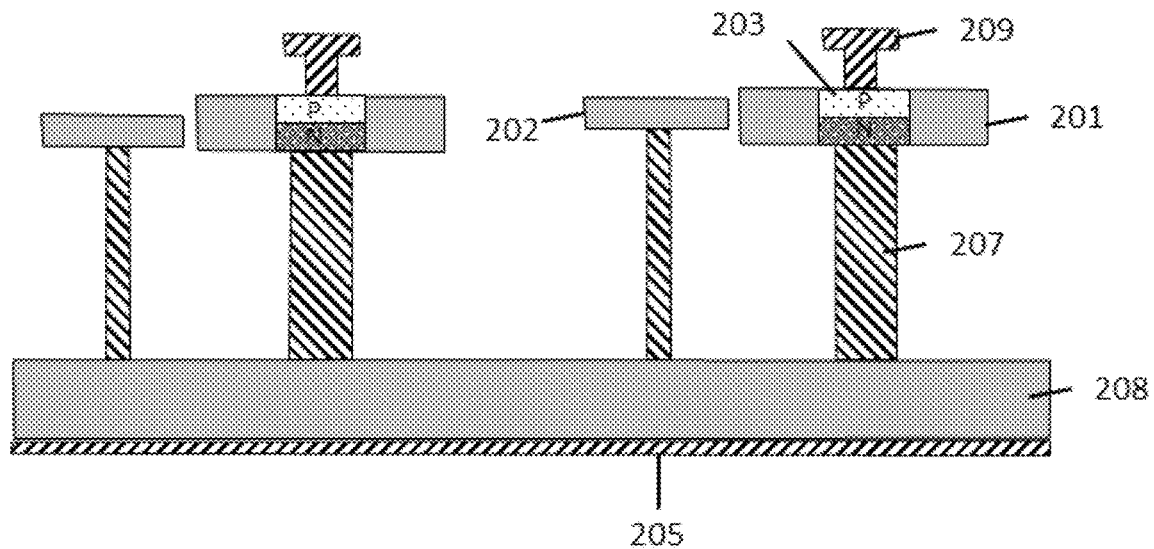
Figure 6-A
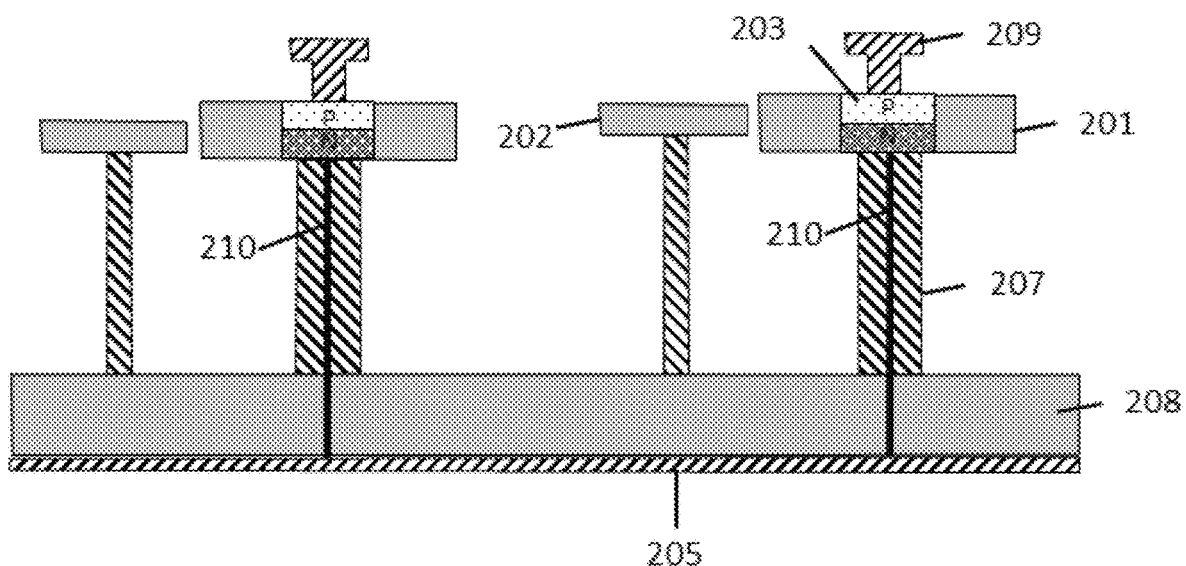
Figure 6-B

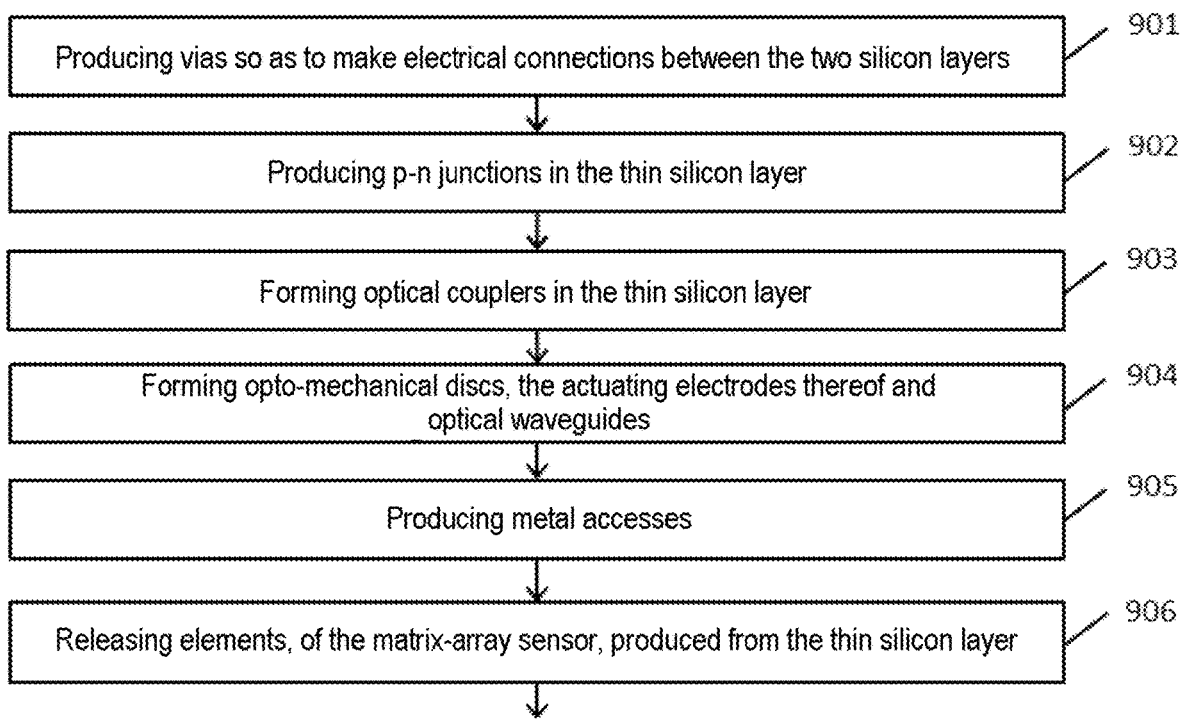
Figure 9
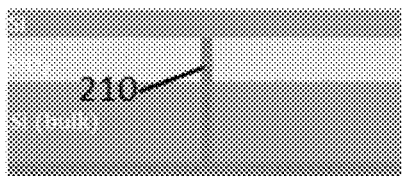
Figure 10-A
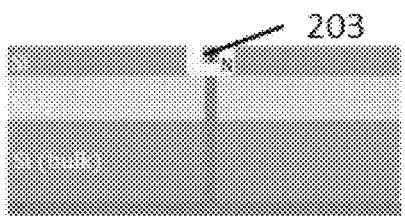
Figure 10-B

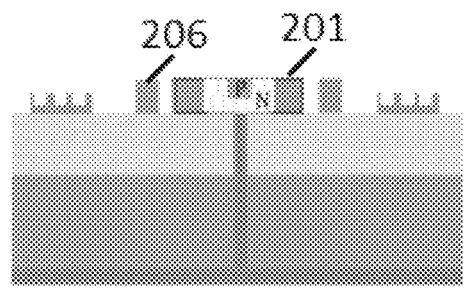
Figure 10-C
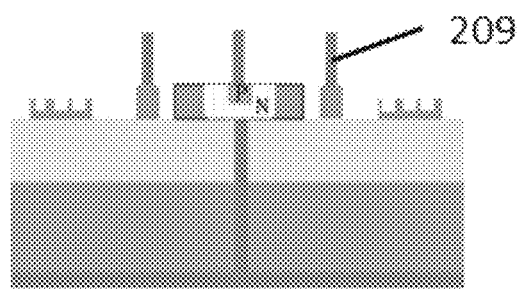
Figure 10-D
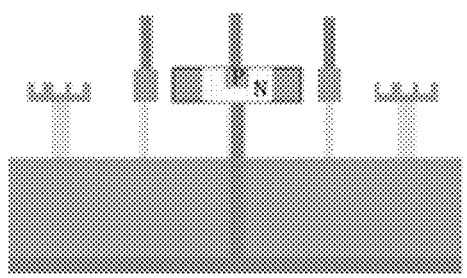
Figure 10-E

DEVICE AND METHOD FOR DETECTING CHEMICAL OR BIOLOGICAL SPECIES

CROSS-REFERENCE TO RELATED APPLICATION

This application claims priority to foreign French patent application No. FR 2110087, filed on Sep. 24, 2021, the disclosure of which is incorporated by reference in its entirety.

FIELD OF THE INVENTION

The present invention generally relates to the field of instrumentation for detecting chemical or biological species, and in particular to a device and method for detecting species. The invention also relates to a process for fabricating such a device.

BACKGROUND

Mass spectrometry is a technique conventionally used to detect and identify chemical or biological species of interest (such as molecules, viruses and bacteria) moving through a liquid or gaseous environment by measuring their mass. In the medical field, mass spectrometry is an effective means for identifying and quantifying the presence of certain types of species in the human body, for example with a view to determining glucose level in the blood, to identifying the presence of certain illicit substances or to detecting tumour markers of certain cancers at very early stages. Devices that implement mass spectrometry are generally expensive, bulky and complex to produce, this greatly restricting deployment and use thereof.

Over the last few years, use of photonics to produce devices implementing mass spectrometry has seen increasing interest. Such interest is explained by the maturity of the technologies required to fabricate light-manipulating devices that meet the constraints in terms of cost and bulk, and by the broad range of applications enabled by light-matter interactions in the context of mass spectrometry. The operating principle of photonic devices implementing mass spectrometry is generally based on the change in the response of an optical component following its interaction with external species. Such a change is quantifiable by analysing the characteristics of an optical signal interacting with such an optical component. By way of example, optical ring micro-resonators are a type of optical resonator that has a high potential as regards detection of species, especially by virtue of its resonant conditions, which depend on the concentration of species in proximity to its active area, the geometry of the active area being a circular annulus encircling the ring micro-resonator. Generally, a layer of active polymer is deposited on the active area of a ring micro-resonator and reacts chemically with species in proximity thereto, thus leading to a change in the resonant conditions of the ring micro-resonator. Despite their efficiency, ring micro-resonators have the drawback of operating indirectly employing as they do an active area located on their circumference, and of having an active area limited to a circular annulus that encircles the resonator but does not cover its interior region, species located in the interior region thus hardly having any effect on the resonant conditions of the ring micro-resonator and therefore remaining undetectable. For example, when the species to be detected is present in a low concentration in the environment of the ring micro-resonator, the narrowness of the active area makes detection difficult to achieve, a measurement time inversely proportional to the concentration of the species of interest being required.

Alternatively to using a ring micro-resonator, it is also known to use an opto-mechanical resonator as species-detecting optical component. Acting as an optical resonator and mechanical resonator in mutual and continuous interaction, opto-mechanical resonators allow, by analysing the shift in the resonant wavelength of the optical resonator, the motion of the mechanical resonator to be determined. Such opto-mechanical coupling is used by the scientific community to detect any species that settles on the surface of the opto-mechanical resonator, as the weight and/or surface stresses of the opto-mechanical resonator and therefore its mechanical resonant frequency are changed thereby. Detection of species by means of an opto-mechanical resonator may thus consist in tracking the shift in the frequency of its mechanical resonance by means of a closed-loop circuit such as a phase-locked loop. However, the performance of opto-mechanical resonators, in terms of sensitivity for example, is highly dependent on their mechanical and optical quality factors. To meet such constraints, opto-mechanical resonators are generally based on an optical micro-cavity the effective length of which is modulated by mechanical vibrations, the optical micro-cavity possibly for example having the geometric shape of a ring, of a disc, of a photonic crystal, etc. Opto-mechanical discs are particularly advantageous as they have a high mechanical quality factor, typically one comprised between 10 and 50, in liquid environments. The quality factor of opto-mechanical discs in liquid environments is for example higher than that allowed by cantilevers, which employ flexural modes of vibration and resonate in a frequency range 10 to 100 times lower. However, the micron-sized dimensions of opto-mechanical discs (radius of a few microns and thickness of about 220 nanometres) are generally negligible with respect to those of the environment in which the species to be detected is found, and their active area is therefore small. Thus, even for a species of interest present in high concentration in the environment of the opto-mechanical disc, a non-negligible measurement time, typically several tens of seconds, is required to detect the species of interest. Measurement time increases as the concentration of the species to be detected decreases. This is a major obstacle to deployment of detecting devices based on opto-mechanical discs, above all in real-time systems requiring almost instantaneous measurements.

U.S. 2016/24600 discloses a device for detecting chemical or biological species comprising a matrix-array of opto-mechanical resonator. Each of these resonators has a different otpical resonance frequency, the resonator being accessed by wavelength multiplexing. The manufacturing of such a device is complex because manufacturing tolerances make it difficult to precisely control the optical resonance frequency of a micrometer-scale resonator.

There is thus a need for an improved device and method for detecting chemical or biological species.

SUMMARY OF THE INVENTION

One subject of the invention is a detecting device configured to detect chemical or biological species in a given environment, the detecting device comprising:
a matrix-array sensor comprising:
a plurality of optical waveguides, a plurality of biasing electrodes and a plurality of actuating electrodes;

a set of opto-mechanical discs arranged in rows and columns, the discs of a given row being optically coupled to the same optical waveguide, each opto-mechanical disc being optically and mechanically resonant and being able to bind to species of the environment, the actuating electrodes being configured to ensure mechanical resonance of the opto-mechanical discs;

a plurality of p-n junctions, each p-n junction being associated with one opto-mechanical disc, the p-n junctions of a given column being electrically connected to the same biasing electrode, each p-n junction being configured to block the flow through the corresponding opto-mechanical disc of a parasitic electrical current originating from a source other than the biasing electrode to which the p-n junction is connected;

an emitting unit comprising at least one laser source configured to generate an optical signal carried at an emission wavelength, the emitting unit further being configured to inject the optical signal into the optical waveguides of the matrix-array sensor;

a control circuit configured to forward bias, during a time window of read-out of a disc of interest, the p-n junction of the disc of interest so as to place, via a thermo-optical effect, its resonant wavelength at a working wavelength, said working wavelength being chosen so that the amplitude of the optical signal propagating through the optical waveguide associated with the disc of interest is modulated by said disc of interest, so as to deliver a modulated optical signal; and a read-out circuit configured to determine on the basis of the modulated optical signal a local detection result, during the time window of read-out of the disc of interest.

Another subject of the invention is a method for detecting chemical or biological species using a plurality of opto-mechanical discs optically coupled to an optical waveguide, the detecting method comprising steps of:

injecting into the optical waveguide an optical signal carried at an emission wavelength, the optical signal being modulated by no opto-mechanical disc;

placing, during a time window of read-out of a disc of interest, the resonant wavelength of the disc of interest at a working wavelength allowing the modulation of the optical signal by the opto-mechanical disc of interest, so as to deliver a modulated optical signal;

determining a local detection result on the basis of the modulated optical signal;

shifting, after the time window of read-out of the disc of interest has passed, the resonant wavelength of the opto-mechanical disc of interest so that the optical signal is not modulated by the opto-mechanical disc of interest; steps b. to d. being reiterated for each of the opto-mechanical discs, so as to deliver a plurality of local detection results.

Yet another subject of the invention is a process for fabricating a matrix-array sensor using a semiconductor wafer comprising a stack of a thick silicon layer, of an insulating layer and of a thin silicon layer, the fabricating process comprising the following steps:

producing vias so as to make electrical connections between the two silicon layers of the wafer;

producing p-n junctions in the thin silicon layer, each p-n junction making contact with one via;

forming optical couplers in the thin silicon layer; forming opto-mechanical discs, the actuating electrodes thereof and optical waveguides;

producing metal accesses to the opto-mechanical discs and to the actuating electrodes;

releasing elements, of the matrix-array sensor, produced from the thin silicon layer.

BRIEF DESCRIPTION OF THE DRAWINGS

Other features and advantages of the present invention will become more clearly apparent on reading the following description with reference to the following appended drawings:

FIG. 2 illustrates operation of an opto-mechanical disc, according to embodiments of the invention;

FIG. 3-A, FIG. 3-B, FIG. 3-C, FIG. 3-D and FIG. 3-E show the variation in the optical response of the opto-mechanical discs, according to one embodiment of the invention;

FIG. 4-A, FIG. 4-B, FIG. 4-C and FIG. 4-D show the variation in the optical response of the opto-mechanical discs, according to another embodiment of the invention;

FIG. 6-A and FIG. 6-B show a cross-sectional view of an opto-mechanical disc, according to two different embodiments of the invention;

FIG. 9 is a flowchart showing a process for fabricating a matrix-array sensor, according to embodiments of the invention; and FIG. 10-A, FIG. 10-B, FIG. 10-C, FIG. 10-D and FIG. 10-E illustrate the output of certain steps of the process for fabricating a matrix-array sensor.

DETAILED DESCRIPTION

Figure 1:
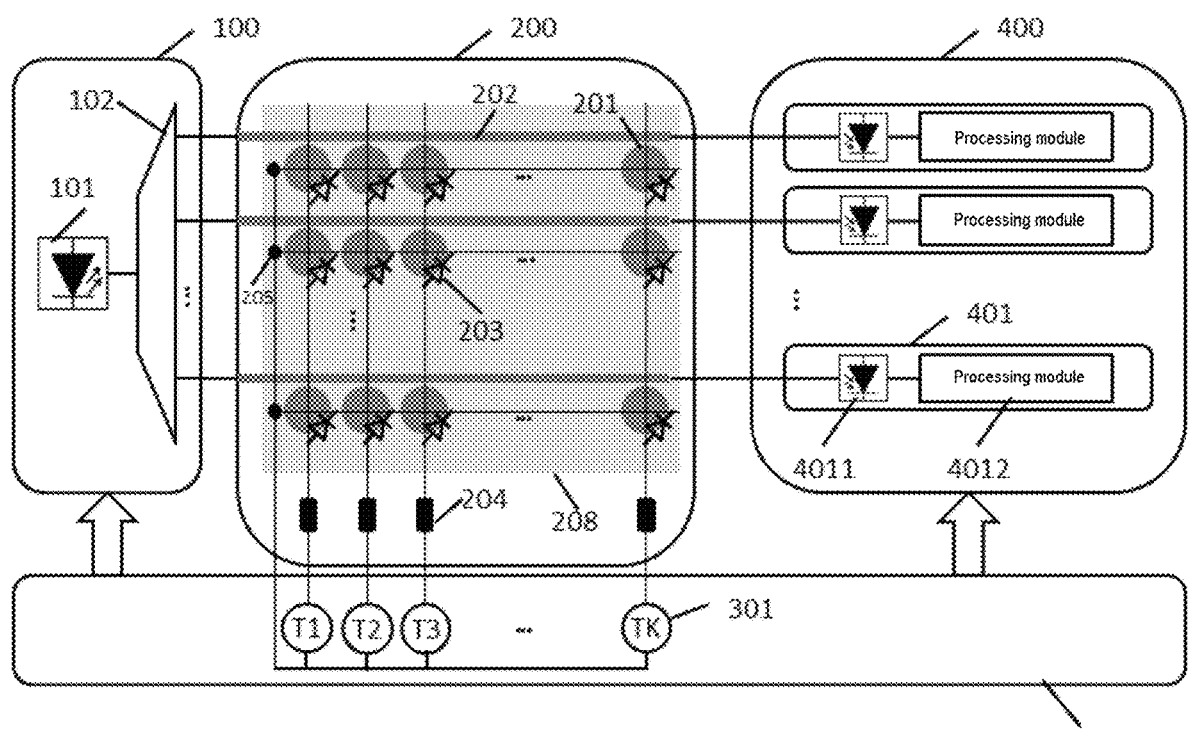
FIG. 1 shows a device for detecting chemical or biological species, according to one embodiment of the invention.

FIG. 1 shows a device 10 for detecting chemical or biological species according to embodiments of the invention. The detecting device 10 may be deployed in a given environment to detect the presence of one or more types of chemical or biological species liable to be moving through the environment in question. The detecting device 10 may further be configured to determine other characteristics related to a detected type of species, such as the concentration in the environment in question of the detected type of species.

The detecting device 10 according to the embodiments of the invention may be deployed in a liquid or gaseous environment. Particles compatible with the detecting device 10 may comprise, for example and non-limitingly, atoms, molecules, ions, proteins, nucleic acids, viruses, etc.

In one example of application of the invention to the medical field, the detecting device 10 may be used to implement blood analyses with a view to determining the concentration in the blood of a given type of species, and for example to determine glucose level (glycaemia) in the blood, to determine the blood group of a patient or to detect the presence of antibodies directed against a given type of virus such as SARS-CoV-2.

In another example of application of the invention, the detecting device 10 may be implemented in monitoring systems intended to trigger alarms depending on the concentration of a type of chemical or biological species in a given environment, such as a system for detecting carbon monoxide in closed environments and a system for evaluating ambient air quality.

As shown in FIG. 1, the detecting device 10 comprises an emitting unit 100, the emitting unit 100 comprising a laser source 101 configured to generate an optical signal at a given emission wavelength. The laser source 101 may not be modulated In this case, characteristics of the generated optical signal (such as its amplitude, its wavelength and its polarization state) remain constant over time.

In one embodiment of the invention, the laser source 101 used in the emitting unit 100 may be a laser source the wavelength of which remains constant over time.

In another embodiment of the invention, the laser source 101 used in the emitting unit 100 may be a wavelength-tunable laser source. In this case, the laser source 101 may be configured to receive a control signal allowing the emission wavelength at which the optical signal is generated to be controlled.

The detecting device 10 further comprises a matrix-array sensor 200, the matrix-array sensor 200 being configured to receive the optical signal generated by the emitting unit 100 via a wired connection or via free space. In the embodiment in which the connection between the emitting unit 100 and the matrix-array sensor 200 is wired, an optical waveguide 202, such as an optical fibre or a waveguide integrated into the substrate, may be used to convey the optical signal from the emitting unit 100 to the matrix-array sensor 200.

The matrix-array sensor 200 may comprise a two-directional arrangement of opto-mechanical discs 201, the opto-mechanical discs 201 being arranged in rows and in columns. The two-directional arrangement of discs 201 may be geometrically regular, i.e. the rows of the matrix-array sensor 200 contain the same number of opto-mechanical discs 201 and the distance separating two neighbouring discs 201 of a given row is equal to the distance separating two neighbouring discs 201 of a given column. The opto-mechanical discs 201 may further be suspended parallel to a common substrate 208 by means of dedicated holders 207.

An opto-mechanical disc 201 will be designated below by $D_{ij}$, the indices i and j designating the ith row and the jth column, of the matrix-array sensor 200, to which the opto-mechanical disc 201 belongs.

Each of the opto-mechanical discs 201 $D_{ij}$ is optically resonant, i.e. an optical signal interacting with the opto-mechanical disc 201 may undergo, when it is characterized in transmission, an attenuation dependent on its wavelength, the attenuation being caused by interference with the incident optical signal after one circuit around the opto-mechanical disc, by absorption and by scattering of light by the opto-mechanical disc. The attenuation is maximum when the wavelength of the optical signal coincides with a resonant wavelength, denoted $\lambda_{res}$, characterizing the opto-mechanical disc 201. The attenuation is minimum in certain ranges of wavelengths of the optical signal, corresponding to an optical signal away from the resonance of the opto-mechanical disc 201. The resonant wavelength $\lambda_{res}$ of a disc 201 $D_{ij}$ depends on a plurality of opto-geometric parameters of the opto-mechanical disc 201, such as for example its radius and its effective refractive index.

Each of the opto-mechanical discs 201 $D_{ij}$ is mechanically resonant, i.e. each disc 201 $D_{ij}$ is subjected to an external modulation that makes its radius vary, the disc 201 therefore being subjected to a succession of expansions and of contractions. The external modulation may be performed with an amplitude that remains constant over time and at a mechanical resonant frequency, denoted $F_m$, that may be as high as a few GHz. Thus, the external modulation of an opto-mechanical disc 201 $D_{ij}$ also modulates its resonant wavelength $\lambda_{res}$, which depends on its radius.

Advantageously, the opto-mechanical discs 201 $D_{ij}$ implemented in the matrix-array sensor 200 may be fabricated from a material or from an alloy of a plurality of materials taking into account the emission wavelength of the laser source 101 and the refractive index of the environment in which the detecting device is intended to be deployed. Generally, the materials from which the opto-mechanical discs 201 are formed must be transparent at the emission wavelength of the laser source 101, while nonetheless allowing a high contrast in index to be obtained with respect to the environment. Furthermore, the geometric characteristics of the opto-mechanical discs 201, i.e. characteristics such as their radius and thickness, may be chosen so as to allow one or more confined optical modes to exist. In one example in which the detecting device 10 operates in the infrared and is intended to be deployed in a gaseous environment, such as ambient air, the opto-mechanical discs 201 may be fabricated based on silicon (refractive index equal to 3.4). In another example in which the detecting device 10 operates in the infrared and is intended to be deployed in a liquid environment, such as water, the opto-mechanical discs 201 may be fabricated based on silicon or based on gallium arsenide (refractive index higher than 4), by way of non-limiting example.

The matrix-array sensor 200 further comprises a plurality of receptors 2011 (shown in FIG. 2) placed substantially uniformly over the detecting face of each of the opto-mechanical discs 201, the detecting face of an opto-mechanical disc 201 being defined as being the face that does not make contact with the holder 207 joining the disc 201 to the common substrate 208. The receptors 2011 are then configured to bind solely to chemical or biological species of interest to be detected by the detecting device 10. The bond between a receptor 2011 and a species of interest may result from forces acting between molecules (ionic bonds, hydrogen bonds and van der Waals forces). When species have become bound to receptors 2011 of an opto-mechanical disc 201, the weight and/or surface stresses change and induce a change in the mechanical resonant frequency of the opto-mechanical disc 201. Moreover, the bond between a receptor 2011 and a species of interest may be reversible, this meaning that it is possible to free the receptors 2011 of their particles by means of a dedicated method without degrading the state of the employed receptors 2011. In the case where the detecting device 10 is intended to detect a single type of species, the receptors 2011 employed in the matrix-array sensor 200 may be identical.

Alternatively, the detecting device 10 may be configured to detect two different types of species. In such an embodiment, the matrix-array sensor 200 may comprise two different types of receptors, each type of receptor 2011 being configured to bind to one different type of species. Advantageously, the sensors of a given type may be placed on the opto-mechanical discs 201 of a given row, in order to facilitate the read-out of the opto-mechanical discs 201. Those skilled in the art will easily understand that the device 10 for detecting chemical or biological species may be configured to detect as many different types of species as there are rows of opto-mechanical discs 201.

The matrix-array sensor 200 further comprises a plurality of optical waveguides 202, each optical waveguide 202 being associated with one row of opto-mechanical discs 201 and being optically coupled to all the discs 201 of the associated row. The optical coupling coefficient of the optical coupling between an optical waveguide 202 and the discs 201 of the associated row may be the same. The optical coupling coefficient between an optical waveguide 202 and an opto-mechanical disc 201 is dependent on the minimum distance separating the waveguide and the disc, this making it difficult to adjust a coupling coefficient after the matrix-array sensor 200 has been fabricated.

The emitting unit 100 may further comprise a distributing optical module 102 configured to inject the optical signal generated by the laser source 101 into one or more optical waveguides 202.

In embodiments of the invention, the distributing optical module 102 may be configured to inject, simultaneously, into each optical waveguide 202 of the matrix-array sensor 200, one portion of the optical signal generated by the laser source 101. For example, the distributing optical module 102 may be a 1×N (one input, N outputs) optical coupler, N being the number of rows of the matrix-array sensor 200. An optical coupler has the advantage of being passive and of not requiring an electrical power supply.

In other embodiments of the invention, the distributing optical module 102 may be configured to inject, at a given time, the entirety of the optical signal generated by the laser source 101 into a row of interest of the matrix-array sensor 200. In this case, the optical module may further be configured to receive a control signal in order to determine the row of interest among the N possible rows. For example, the distributing optical module 102 may be a 1×N (one input, N outputs) optical switch. Such embodiments are particularly advantageous in the case where the number of rows of the matrix-array sensor 200 is high, typically higher than 20.

The matrix-array sensor 200 comprises a plurality of biasing electrodes 204, each biasing electrode 204 being associated with one column of the matrix-array sensor 200. Furthermore, the opto-mechanical discs 201 belonging to the same column may be electrically connected to the associated biasing electrode 204 by means of a metal conductor 209 that may be based on copper, for example. The matrix-array sensor 200 further comprises an electrode 205 that is common to all the opto-mechanical discs 201 employed in the matrix-array sensor 200. Advantageously, the common electrode 205 may be arranged in the matrix-array sensor 200 so as to allow flow, through the opto-mechanical discs 201 of any column of the matrix-array sensor 200, of an electrical current generated by an electrical potential difference between the biasing electrode 204 associated with the column and the common electrode 205. When an electrical current passes through an opto-mechanical disc 201, the disc 201 gets hotter and its refractive index varies. As a result, the resonant wavelength of the opto-mechanical disc 201 shifts.

The matrix-array sensor 200 further comprises a plurality of p-n junctions 203, each p-n junction 203 being associated with one opto-mechanical disc 201 and comprising a p-doped region and an n-doped region. Furthermore, each p-n junction 203 of an opto-mechanical disc 201 may be arranged in the matrix-array sensor 200 so that its p-doped region is electrically connected to the biasing electrode 204 associated with the opto-mechanical disc 201 and so that its n-doped region is electrically connected to the common electrode 205. Such a configuration has the advantage of allowing flow through the opto-mechanical disc 201 of any electrical current originating from the biasing electrode 204 associated with the disc 201 (forward bias of the p-n junction 203), and of blocking flow through the opto-mechanical disc 201 of any parasitic electrical current originating from other sources, and in particular of the parasitic electrical currents originating from the common electrode 205 (reverse bias of the p-n junction 203). Thus, considering the opto-mechanical discs 201 of a row of interest of the matrix-array sensor 200, it is possible, by forward biasing the p-n junction 203 of an opto-mechanical disc of interest 201, to shift its resonant wavelength without the other discs 201 of the row of interest being passed through by parasitic electrical currents. By independently forward biasing the p-n junction 203 of each of the opto-mechanical discs 201, it is possible to separately shift the resonant wavelengths of the opto-mechanical disc 201 of each row of the matrix-array sensor 200. Thus, it is possible to configure the discs 201 of a row of interest so that a single disc 201 of the row interacts with the optical signal injected into the optical waveguide 202, the optical signal being off resonance for the other discs 201 of the row. This makes it possible to obtain, at the output of the optical waveguide 202, an exploitable optical signal, i.e. an optical signal that is detectable by a photodetector 4011. Such a feature of the detecting device 10 is particularly advantageous when the number of opto-mechanical discs 201 arranged in each row is high, typically higher than 50.

Prior-art solutions in respect of control, via a thermo-optical effect, of the resonant conditions of an optical or opto-mechanical resonator generally employ a resistive heater located in proximity to the resonator to be controlled. Despite the better efficiency obtained with a configuration comprising a single resonator such as described in [1], such a solution is incompatible with an array of resonators in which a significant number, higher than 100 for example, of resonators are arranged over an integration area of a few centimetres square. Specifically, the symmetric nature of the resistive heater, which lets electrical currents pass in both directions, promotes the appearance of parasitic electrical currents in the array of resonators. Such parasitic electrical currents disrupt the operation of the array of resonators by arbitrarily modifying the resonant conditions of certain employed optical resonators. Moreover, the resistive heater is generally separated from the resonator to be controlled by a stack of a plurality of layers of semiconductors and/or metals, this meaning that a high electrical power is required to control the resonant conditions of the resonator using prior-art solutions.

FIG. 2 illustrates operation of an opto-mechanical disc 201, according to embodiments of the invention. The optical response of the opto-mechanical disc 201 has a Lorentzian shape associated with a maximum attenuation at the resonant wavelength and with two edges: a rising edge and a falling edge. The resonant wavelength of the opto-mechanical disc 201 may be set beforehand, for example in a static regime without external modulation, at a working wavelength, the working wavelength being chosen so that the wavelength of the input optical system remains on the same, rising or falling, edge during the oscillation of the optical response of the disc 201, i.e. in a dynamic regime with the external modulation. In a dynamic regime consisting in subjecting the opto-mechanical disc 201 to an external modulation, at the mechanical resonant frequency $F_m$, in order to make it vibrate, the optical response of the opto-mechanical disc 201 oscillates at the same rate, i.e. at the mechanical resonant frequency $F_m$. In particular, the resonant wavelength of the opto-mechanical disc 201 oscillates between a minimum resonant wavelength and a maximum resonant wavelength. In this case, the attenuation undergone by the input optical signal (equivalent to the loss generated by the disc) varies almost linearly in each half-period of oscillation of the optical response of the disc, the output optical signal thus being amplitude modulated. Optionally, the working wavelength may further be optimized so as to maximize the optical power of the optical signal output. In one embodiment, the external modulation applied to the opto-mechanical disc 201 may be performed by means of two actuating electrodes 206 that encircle the opto-mechanical disc 201 and that are connected to a generator 302 of radio-frequency signals. In this case, the two actuating electrodes 206 generate an electrostatic actuating force allowing a vibration of the opto-mechanical disc 201 to be driven.

Advantageously, the matrix-array sensor 200 may further comprise a plurality of actuating electrodes 206 (not shown in FIGS. 1 and 5), each of the opto-mechanical discs 201 of the matrix-array sensor 200 being encircled by at least two actuating electrodes 206 such as described with reference to FIG. 2. The control circuit 300 further comprises a generator 302 of radio-frequency signals that is configured to deliver to the actuating electrodes 206 encircling each disc 201 a modulation signal allowing each opto-mechanical disc 201 to be subjected to an electrostatic actuating force that drives its vibration.

The detecting device 10 further comprises a control circuit 300 configured to control the operation of one or more constituent elements of the detecting device 10. Such constituent elements may comprise the matrix-array sensor 200 and the emitting unit 100. The control circuit 300 comprises adjustable voltage sources 301 that may correspond in number to the number of columns in the matrix-array sensor 200, each adjustable voltage source 301 being able to be connected to the biasing electrode 204 of a corresponding column in the matrix-array sensor 200 and to the common electrode 205. In the case where the distributing optical module 102 provided in the emitting unit 100 is an optical switch, the control circuit 300 may be configured to transmit to the distributing optical module 102, prior to the time windows of read-out of the discs 201 of a row of interest, a control signal allowing an optical signal to be injected into the optical waveguide 202 of the row of interest.

In embodiments of the invention where the laser source 101 employed in the emitting unit 100 is not wavelength-tunable, the control circuit 300 may be configured to implement, prior to the time windows of read-out of the discs 201 of a row of interest, a first step of shifting the resonant wavelength of one or more discs 201 belonging to the row of interest so as to place the optical signal propagating through the optical waveguide 202 away from the resonance of each of the discs of the row of interest, that is so that no disc 201 of the row of interest modulates the optical signal propagating through the optical waveguide 202. The control circuit 300 may be configured to then implement a second step of placing, during a time window of read-out of a disc of interest 201 belonging to the row of interest, the resonant wavelength of the disc of interest 201 at a working wavelength allowing the amplitude of the optical signal to be modulated such as described with reference to FIG. 2. The disc of interest 201 is subjected to an external modulation, so as to deliver an amplitude-modulated optical signal to the output of the optical waveguide 202. After the time window of read-out of the disc of interest 201 has passed, the control circuit 300 may be configured to again implement the first step in order to place the optical signal propagating through the optical waveguide 202 away from the resonance of each of the discs of the row of interest. Advantageously, the control circuit 300 may be configured to implement a plurality of iterations, each iteration comprising one execution of the first and second steps, in order to allow other discs 201 of the row of interest to be read out, the read-out being carried out individually and sequentially over time. FIGS. 3-A to 3-B illustrate, by way of example, adjustment of the resonant wavelengths of the opto-mechanical discs 201 of a row of interest in order to allow the read-out of all the discs 201 of the row of interest, according to such embodiments. More precisely, FIG. 3-A corresponds to an initial state of the opto-mechanical discs 201, in which state the resonant wavelengths of the discs 201 are arbitrarily dispersed over a broad spectrum of wavelengths, the emission wavelength of the laser source 101 being, for example and non-limitingly, subjected to the attenuation of one or more opto-mechanical discs 201. FIG. 3-B illustrates the configuration of the resonant wavelengths of the discs 201 after implementation by the control circuit of the first step described above of placing off resonance the optical signal generated by the laser source by shifting the resonant wavelength of one or more opto-mechanical discs 201 by biasing the one or more corresponding p-n junctions. FIG. 3-C corresponds to the configuration of the resonant wavelengths of the discs 201 after implementation of the second step described above of placing, during a time window of read-out of a disc of interest, the resonant wavelength of the disc of interest at a working wavelength such as described with reference to FIG. 2. FIGS. 3-D and 3-E corresponding to a new iteration of the first and second steps implemented by the control circuit 300 in order to allow another opto-mechanical disc 201 belonging to the row of interest to be read out. Such embodiments have the advantage of using a laser source 101 that is not wavelength-tunable.

In other embodiments of the invention where the laser source 101 employed in the emitting unit 100 is wavelength-tunable, the control circuit 300 may be configured to implement, prior to the time windows of read-out of the discs 201 of a row of interest, a first step of defining the emission wavelength of the laser source 101 so as to place the optical signal propagating through the optical waveguide 202 away from the resonance of each of the discs of the row of interest, that is so that no disc 201 of the row of interest modulates the optical signal propagating through the optical waveguide 202. The control circuit 300 may be configured to then implement the second step described above of placing, during a time window of read-out of a disc of interest 201 belonging to the row of interest, the resonant wavelength of the disc of interest 201 at a working wavelength allowing the amplitude of the optical signal to be modulated such as described with reference to FIG. 2. After the time window of read-out of the disc of interest 201 has passed, the control circuit 300 may be configured to again implement a third step of placing the optical signal propagating through the optical waveguide 202 away from the resonance of each of the discs of the row of interest. Advantageously, the control circuit 300 may be configured to implement a plurality of iterations, each iteration comprising one execution of the second and third steps, in order to allow other discs 201 of the row of interest to be read out, the read-out being carried out individually and sequentially over time. FIGS. 4-A to 4-D illustrate, by way of example, adjustment of the resonant wavelengths of the opto-mechanical discs 201 of a row of interest in order to allow the read-out of all the discs 201 of the row of interest, according to such embodiments. More precisely, FIG. 4-A corresponds to an initial state of the opto-mechanical discs 201. FIG. 4-B illustrates the shift of emission wavelength of the laser source 101 in the first step described above. FIG. 4-C corresponds to the configuration of the resonant wavelengths of the discs 201 after implementation of the second step described above of placing, during a time window of read-out of a disc of interest, the resonant wavelength of the disc of interest at a working wavelength such as described with reference to FIG. 2. FIG. 4-D corresponds to the configuration of the resonant wavelengths of the discs 201 after implementation of the third step described above. Such embodiments have the advantage of requiring a single p-n junction 203 to be biased in each time window of read-out of a disc of interest 201.

As illustrated in FIG. 1, the detecting device 10 further comprises a read-out circuit 400 configured to receive each modulated optical signal after propagation through the associated optical waveguide 202. The read-out circuit 400 may comprise a plurality of read-out units 401, each of the read-out units 401 being associated with one optical waveguide 202 and comprising one photodetector 4011 and one processing module 4012. The photodetector 4011 is configured to convert the received modulated optical signal into the electrical domain, so as to deliver an electrical detection signal The processing module 4012 is configured to determine a local detection result on the basis of the characteristics of the electrical detection signal.

Advantageously, operation of a processing module 4012 may be controlled by the control circuit 300 employed in the detecting device 10. In such an embodiment, the control circuit 300 may be configured, during a time window of read-out of a disc of interest 201, to place the resonant wavelength of the disc of interest 201 at a working wavelength such as described with reference to FIG. 2, and to trigger determination of a local detection result by the processing module 4012 associated with the same row as the disc of interest 201. For example, the processing module 4012 may be configured, in response to receipt of an electrical detection signal, to implement steps of:
- determining the modulation frequency $F_{output}$ of the electrical detection signal;
- computing a frequency difference $\Delta F$ between the modulation frequency $F_{output}$ and a reference frequency $F_{ref}$;
- determining the local detection result on the basis of the frequency difference $\Delta F$.

The reference frequency $F_{ref}$ is the mechanical resonant frequency of the opto-mechanical disc of interest 201 when no species is bound to its receptors 2011. The modulation frequency $F_{output}$ is the mechanical resonant frequency of the opto-mechanical disc of interest 201 when species are liable to be bound to its receptors 2011. Generally, the frequency difference $\Delta F$ is proportional to the weight of the species bound to the receptors 2011 of the disc of interest 201.

In embodiments of the invention, the device 10 for detecting chemical or biological species may be configured to implement a sequential read-out of the rows of the matrix-array sensor 200, so as to deliver for each row of the matrix-array sensor 200 a plurality of local detection results. The detecting device 10 may further be configured to determine a global detection result on the basis of the plurality of local detection results thus determined. For each row of the matrix-array sensor 200, the detecting device 10 may be configured to carry out a sequential read-out of the opto-mechanical discs 201 by implementing steps of:
a. injecting into the optical waveguide 202 of the row an optical signal carried at an emission wavelength, the optical signal being modulated by no opto-mechanical disc 201 of the row;
b. placing, during a time window of read-out of a disc of interest 201, the resonant wavelength of the disc of interest 201 at a working wavelength allowing the modulation of the optical signal by the opto-mechanical disc of interest 201, so as to deliver a modulated optical signal;
c. determining a local detection result on the basis of the modulated optical signal;
d. shifting, after the time window of read-out of the disc of interest 201 has passed, the resonant wavelength of the opto-mechanical disc of interest 201 so that the optical signal is not modulated by the opto-mechanical disc of interest 201.

The detecting device 10 may be configured to implement steps b. to d. for each of the opto-mechanical discs 201 of the line, so as to deliver the plurality of local detection results, these being obtained in a short space of time.

In one embodiment, the detecting device 10 may be configured to implement a prior calibration phase consisting in determining the reference frequency $F_{ref}$ of each of the opto-mechanical discs 201 employed in the matrix-array sensor 200, the reference frequency $F_{ref}$ of an opto-mechanical disc 201 being its mechanical resonant frequency when no particle is bound to its receptors 2011.

Figure 5:
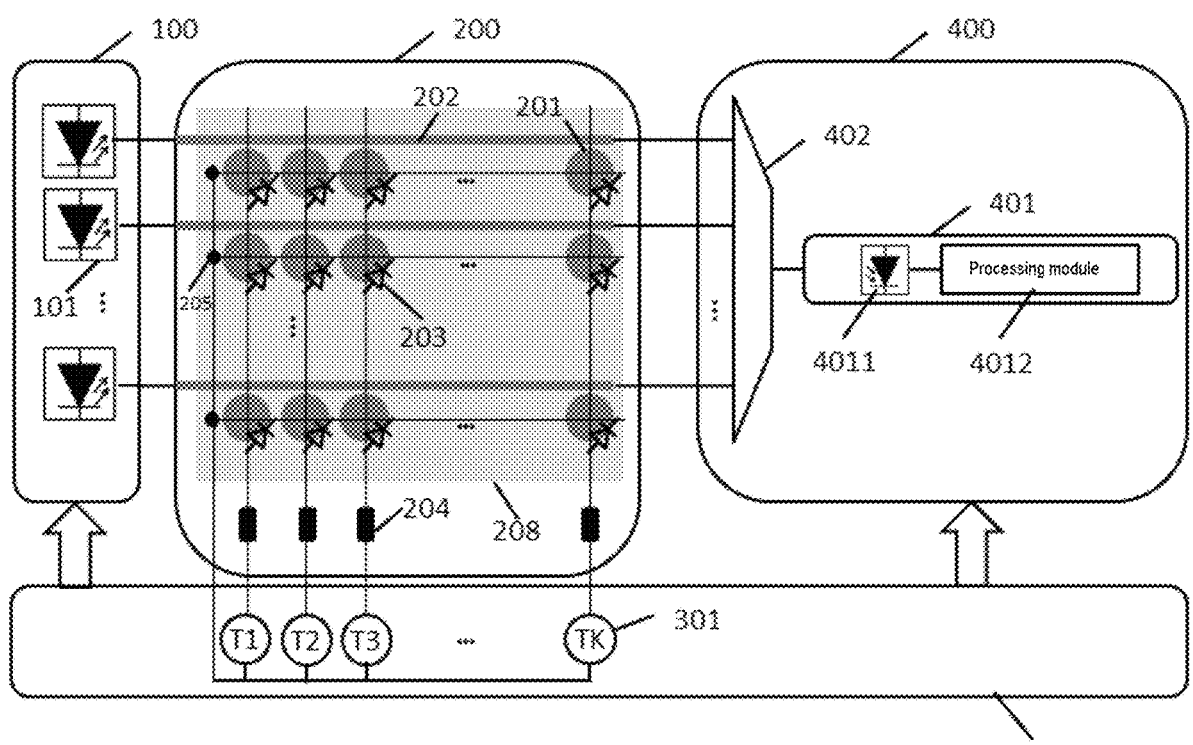
FIG. 5 shows a device for detecting chemical or biological species, according to another embodiment of the invention.

FIG. 5 shows a device 10 for detecting chemical or biological species, according to another embodiment of the invention. In such an embodiment, the emitting unit 100 may comprise a plurality of laser sources 101. For example, the number of laser sources 101 may be equal to the number of rows of the matrix-array sensor 200. In this case, each laser source 101 is optically coupled to a single optical waveguide 202. The laser sources 101 may be wavelength-tunable, the emission wavelength of each of the laser sources 101 being determined by the employed control circuit 300 through delivery of control signals. Use of a plurality of laser sources 101 in the emitting unit 100 allows the distributing optical module 102 to be omitted.

As illustrated in FIG. 5, the read-out circuit 400 may comprise a single read-out unit 401. In such an embodiment, the detecting device 10 further comprises an N×1 (N inputs, one output) optical switch 402 controlled by the control circuit 300, each optical input of the switch being connected to the output of a corresponding optical waveguide 202 and the output of the optical switch being connected to the optical input of the photodetector 4011 employed in the read-out unit 401. The control circuit 300 may be configured to connect, during a time window of read-out of a disc of interest 201, the output of the optical waveguide 202 associated with the disc of interest 201 to the read-out unit 401, by means of the optical switch.

FIG. 6-A shows an opto-mechanical disc 201 and the corresponding p-n junction 203, according to one embodiment of the invention. The p-n junction 203 is produced by doping a central region of the opto-mechanical disc 201, the doped central region having a cylindrical shape and its radius being smaller than that of the opto-mechanical disc 201. For example, the radius of the doped central region may be comprised between 50% and 90% of the radius of the opto-mechanical disc 201. The p-doped region of the p-n junction 203 may be produced so that it opens onto the detection face of the opto-mechanical disc 201. The n-doped region of the p-n junction 203 may be produced so as to cover the entire area of contact between the disc 201 and the disc holder 207.

FIG. 6-B shows an opto-mechanical disc 201 and the corresponding p-n junction 203, according to another embodiment of the invention. In comparison with the structure described with reference to FIG. 6-A, the structure of FIG. 6-B further comprises vias 210. Each via 210 is associated with one opto-mechanical disc 201 and makes an electrical connection between the disc 201 and the corresponding common electrode 205.

Figure 7:
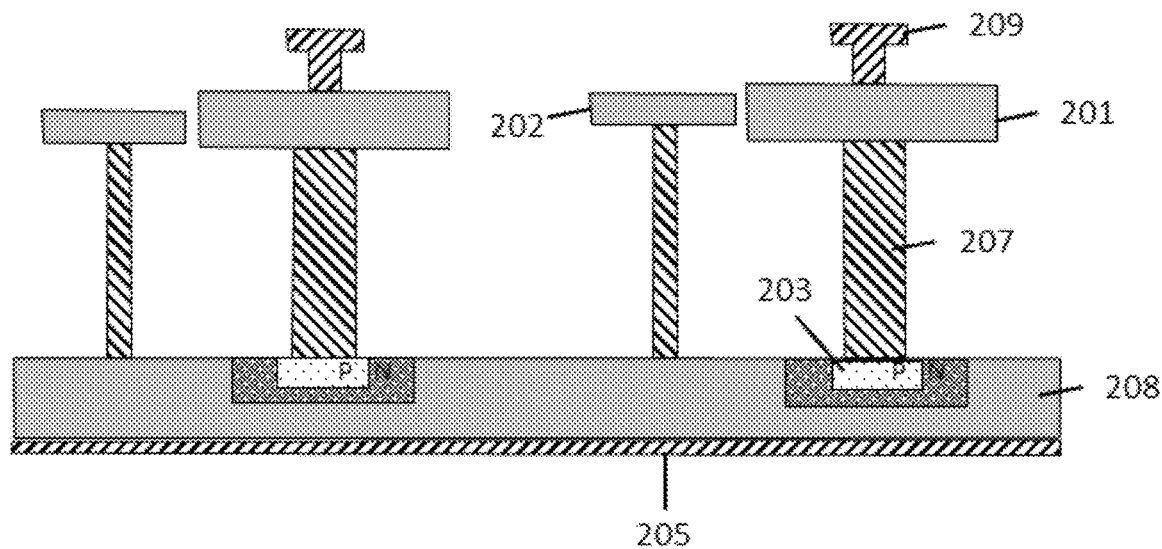
FIG. 7 shows a cross-sectional view of an opto-mechanical disc, according to other embodiments of the invention.

FIG. 7 shows an opto-mechanical disc 201 and the corresponding p-n junction 203, according to other embodiments of the invention. In such embodiments, the p-n junction 203 associated with an opto-mechanical disc 201 is produced by doping the common substrate 208 on which the holder 207 allowing the opto-mechanical disc 201 to be suspended is placed. The p-doped region of the p-n junction 203 may be produced so as to cover the entire area of contact between the holder 207 of the opto-mechanical disc 201 and the common substrate 208. The n-doped region may be produced so as to contain the p-doped region.

Figure 8:
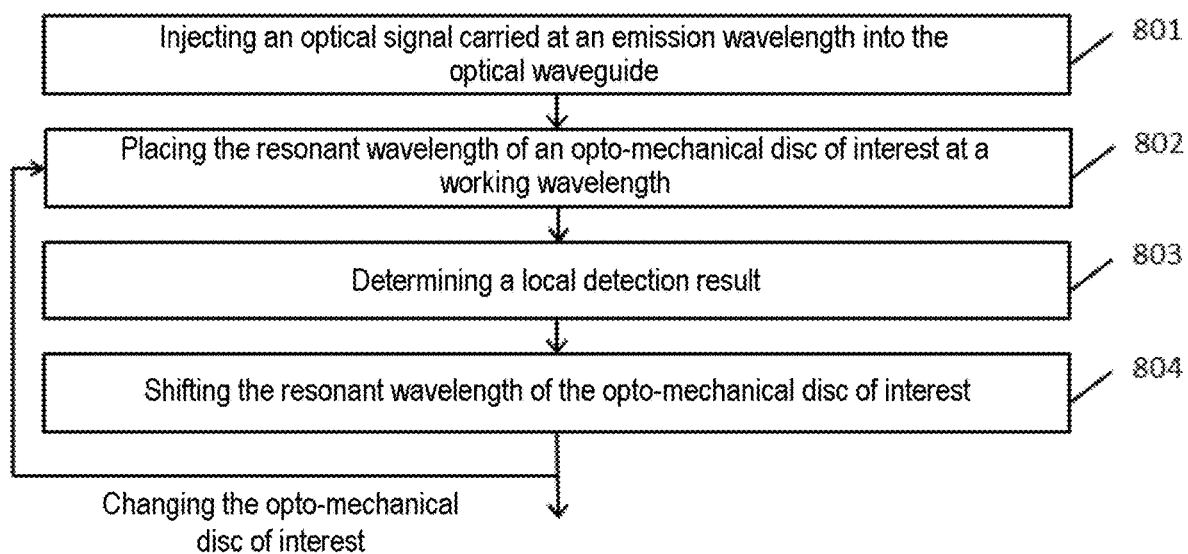
FIG. 8 is a flowchart showing a method for detecting chemical or biological species, according to embodiments of the invention.

FIG. 8 shows a method for detecting chemical or biological species using a plurality of opto-mechanical discs 201 optically coupled to an optical waveguide 202, according to embodiments of the invention. The detecting method implements the steps 801 to 804.

In step 801, an optical signal carried at an emission wavelength is injected into the optical waveguide 202, the optical signal being modulated by no opto-mechanical disc 201 of the row. Such a configuration may be obtained by shifting the resonant wavelength of one or more discs 201 and/or by adjusting the emission wavelength of the laser source 101 generating the optical signal.

In step 802, the resonant wavelength of an opto-mechanical disc of interest 201 is set, during a time window of read-out of the disc of interest 201, at a working wavelength allowing the modulation of the optical signal by the opto-mechanical disc of interest 201, so as to deliver a modulated optical signal.

In step 803, a local detection result is determined on the basis of the modulated optical signal. For example, the local detection result may be determined by comparing, with a reference frequency $F_{ref}$, the modulation frequency $F_{output}$ of an electrical detection signal obtained by converting the modulated optical signal into the electrical domain.

In step 804, the resonant wavelength of the opto-mechanical disc of interest 201 is shifted, after the time window of read-out of the disc of interest 201 has passed, so that the optical signal is not modulated by the opto-mechanical disc of interest 201.

Steps 802 to 804 may be reiterated for each of the opto-mechanical discs 201, so as to deliver a plurality of local detection results.

FIG. 9 shows a process for fabricating a matrix-array sensor 200, according to embodiments of the invention. The fabricating process uses a silicon-on-insulator (SOI) wafer comprising a stack of a thin silicon layer (Si) of about 220 nm thickness on an insulating layer that may, for example and non-limitingly, be of silicon dioxide ($SiO_2$), the stack further comprising a thick silicon layer (Si bulk) that completes the stack on the other side of the insulating layer. In 200 mm technology, the thickness of this layer is about 725 µm, but it may be thinner, and as thin as a few µm.

In step 901, vias 210 are produced so as to make electrical connections between the two silicon layers of the wafer. Step 901 further consists in producing a common electrode 205 by metallization of the back side of the thick silicon layer. FIG. 10-A illustrates the output of step 901.

In step 902, p-n junctions 203 are produced in the thin silicon layer, each p-n junction 203 being produced so as to make contact with one via. More precisely, step 902 may consist in implanting phosphorous and boron locally to produce the n-doped and p-doped regions of each p-n junction 203, respectively. FIG. 10-B illustrates the output of step 902.

In step 903, optical couplers forming the terminations of each optical waveguide 202 are formed in order to ensure out-of-plane coupling to optical fibres. To do this, step 903 may consist in implementing fabricating steps comprising an optical or e-beam lithography step carried out by means of a dedicated mask on a resist layer deposited on the thin silicon layer, a developing step in order to free regions to be etched, and a step of partial etching of the thin silicon layer to achieve a refractive-index modulation, the etching preferably being dry etching. The thickness etched, measured in a direction perpendicular to the stacking plane of the semiconductor layers, may represent about one third of the thickness of the thin silicon layer (about 70 nm for a thin silicon layer of about 220 nm).

In step 904, opto-mechanical discs 201, the actuating electrodes 206 thereof and optical waveguides are formed. More precisely, step 904 may consist in implementing fabricating steps comprising an optical or e-beam lithography step carried out by means of a dedicated mask on a resist layer deposited on the thin silicon layer, a developing step to free regions to be etched, and a step of etching the thin silicon layer, the thin silicon layer being completely etched, i.e. until the insulating layer is reached. FIG. 10-C illustrates the output of step 904.

In step 905, metal accesses 209 to the opto-mechanical discs 201 and to the actuating electrodes 206 are produced. To do this, step 905 may consist in implementing fabricating steps comprising a lithography step carried out by means of a dedicated mask on a resist layer deposited on the thin silicon layer, a developing step in order to free the sites of the metal accesses, and a step of depositing a target material (generally a metal) that forms the metal accesses. FIG. 10-D illustrates the output of step 905.

In step 906, elements of the matrix-array sensor 200 produced from the thin silicon layer are released, i.e. become suspended by means of the remainder of the insulating layer. Such released elements comprise the opto-mechanical discs 201 and the optical waveguides 202. The release may be achieved by means of a chemical etch using vapour-phase hydrofluoric acid. FIG. 10-E illustrates the output of step 906.

The invention is not limited to the embodiments described above by way of non-limiting example and variants are possible. For example:

In embodiments of the invention, the two-directional arrangement of opto-mechanical discs 201 in the matrix-array sensor 200 may be geometrically irregular, i.e. the number of discs 201 and the distance separating two neighbouring discs 201 may vary from one row to another and/or from one column to another.

In other embodiments of the invention, the laser source 101 employed in the emitting unit 100 may be a multi-mode laser source. In this case, the optical signal generated by the laser source 101 is carried at a plurality of emission wavelengths. In such embodiments of the invention, the optical distributing module 102 employed in the emitting unit 100 may be an arrayed waveguide grating (AWG), the AWG being configured to inject into each optical waveguide 202 of the matrix-array sensor 200 one filtered optical signal carried at one emission wavelength.

In embodiments of the invention where the laser source 101 employed in the emitting unit 100 is wavelength-tunable, the control circuit 300 may be configured to adjust, prior to the time windows of read-out of the discs 201 of a row of interest, the emission wavelength at which is carried the optical signal injected into the optical waveguide 202 of the row of interest and to shift the resonant wavelength of one or more discs 201 of the row of interest so that the optical signal is modulated by no disc 201 of the row of interest.

In other embodiments of the invention, the matrix-array sensor 200 may be produced on a photonic integration platform such as a silicon platform. The advantages of such an integrated-photonic embodiment include miniaturization, compactness, and a low power consumption and a low cost of fabrication.

REFERENCES

[1] "A Temperature Controller IC for Maximizing Si Micro-Ring Modulator Optical Modulation Amplitude" Min-Hyeong Kim and al., JOURNAL OF LIGHTWAVE TECHONOLOGY, 2019

The invention claimed is:

1. A detecting device configured to detect chemical or biological species in a given environment, the detecting device comprising:
   a matrix-array sensor comprising:
   a plurality of optical waveguides, a plurality of biasing electrodes and a plurality of actuating electrodes;
   a set of opto-mechanical discs arranged in rows and columns, the discs of a given row being optically coupled to the same optical waveguide, each opto-mechanical disc being optically and mechanically resonant and being able to bind to species of the environment, the actuating electrodes being configured to ensure mechanical resonance of the opto-mechanical discs;
   a plurality of p-n junctions, each p-n junction being associated with one opto-mechanical disc, the p-n junctions of a given column being electrically connected to the same biasing electrode, each p-n junction being configured to block the flow through the corresponding opto-mechanical disc of a parasitic electrical current originating from a source other than the biasing electrode to which the p-n junction is connected;
   an emitting unit comprising at least one laser source configured to generate an optical signal carried at an emission wavelength, the emitting unit further being configured to inject the optical signal into the optical waveguides of the matrix-array sensor;
   a control circuit configured to forward bias, during a time window of read-out of a disc of interest, the p-n junction of the disc of interest so as to place, via a thermo-optical effect, its resonant wavelength at a working wavelength, said working wavelength being chosen so that the amplitude of the optical signal propagating through the optical waveguide associated with the disc of interest is modulated by said disc of interest, so as to deliver a modulated optical signal; and
   a read-out circuit configured to determine on the basis of the modulated optical signal a local detection result, during the time window of read-out of the disc of interest.

2. The detecting device according to claim 1, wherein the emitting unit comprises a single laser source, the emitting unit further comprising a distributing optical module configured to simultaneously inject the optical signal generated by the laser source into one or more optical waveguides of the matrix-array sensor.

3. The detecting device according to claim 1, wherein the emitting unit comprises a plurality of laser sources, the number of laser sources being equal to the number of optical waveguides in the matrix-array sensor, the emitting unit being configured to inject the optical signal generated by each laser source into a corresponding optical waveguide in the matrix-array sensor.

4. The detecting device according to claim 1, wherein the control circuit is configured to shift, prior to the time windows of read-out of the discs of a row of interest, the resonant wavelength of one or more discs belonging to the row of interest so that the optical signal propagating through the optical waveguide associated with the row of interest is modulated by no disc.

5. The detecting device according to claim 1, wherein the laser sources of the emitting unit are wavelength-tunable, the control circuit further being configured to determine the emission wavelength of each of the laser sources.

6. The detecting device according to claim 5, wherein the control circuit is configured to adjust, prior to the time windows of read-out of the discs of a row of interest, the emission wavelength of the laser source associated with the row of interest so that the optical signal propagating through the optical waveguide associated with the row of interest is modulated by no disc.

7. The detecting device according to claim 1, wherein at least one p-n junction of an opto-mechanical disc is arranged in a central region of the corresponding opto-mechanical disc.

8. The detecting device according to claim 1, wherein each opto-mechanical disc is suspended by means of a holder placed on a common substrate.

9. The detecting device according to claim 8, wherein at least one p-n junction of an opto-mechanical disc is arranged in the region, of the common substrate, on which the holder of the opto-mechanical disc is placed.

10. The detecting device according to claim 1, wherein the control circuit comprises a plurality of adjustable voltage sources, each adjustable voltage source being configured to apply an electrical potential difference between a biasing electrode and a common electrode so as to forward bias the p-n junctions associated with the biasing electrode.

11. The detecting device according to claim 1, wherein the read-out circuit comprises at least one read-out unit, the read-out unit comprising a photodetector configured to convert the modulated optical signal into an electrical detection signal, the read-out unit further comprising a processing module configured, during the time window of read-out of the disc of interest, to:
   determine a modulation frequency ($F_{output}$) of the electrical detection signal;
   compute a frequency difference ($\Delta F$) between the modulation frequency ($F_{output}$) and a reference frequency ($F_{ref}$);
   determine the local detection result on the basis of the frequency difference ($\Delta F$).

12. The detecting device according to claim 1, wherein the detecting device is configured to carry out a sequential read-out of the rows of the matrix-array sensor, so as to deliver for each row of the matrix-array sensor a plurality of local detection results, the detecting device further being configured to determine a global detection result on the basis of the plurality of local detection results.

13. A method for detecting chemical or biological species using a plurality of opto-mechanical discs optically coupled to an optical waveguide, the detecting method comprising steps of:
   a. injecting into the optical waveguide an optical signal carried at an emission wavelength, the optical signal being modulated by no opto-mechanical disc;

b. placing, during a time window of read-out of a disc of interest, the resonant wavelength of the disc of interest at a working wavelength allowing the modulation of the optical signal by the opto-mechanical disc of interest, so as to deliver a modulated optical signal;
c. determining a local detection result on the basis of the modulated optical signal;
d. shifting, after the time window of read-out of the disc of interest has passed, the resonant wavelength of the opto-mechanical disc of interest so that the optical signal is not modulated by the opto-mechanical disc of interest;

steps b. to d. being reiterated for each of the opto-mechanical discs, so as to deliver a plurality of local detection results.

14. A process for fabricating a matrix-array sensor using a semiconductor wafer comprising a stack of a thick silicon layer, of an insulating layer and of a thin silicon layer, the fabricating process comprising the following steps:

producing vias so as to make electrical connections between the two silicon layers of the wafer;

producing p-n junctions in the thin silicon layer, each p-n junction making contact with one via;

forming optical couplers in the thin silicon layer;

forming opto-mechanical discs, the actuating electrodes thereof and optical waveguides;

producing metal accesses to the opto-mechanical discs and to the actuating electrodes;

releasing elements, of the matrix-array sensor, produced from the thin silicon layer.

\* \* \* \* \*